United States Patent [19]

Wu et al.

[11] 4,217,291

[45] Aug. 12, 1980

[54] METHOD OF OXIDIZING OSMIUM (III) AND OSMIUM (IV) TO A HIGHER VALENCY STATE

[75] Inventors: Ching-Yong Wu, O'Hara Township, Allegheny County; Thaddeus P. Kobylinski, Gibsonia, both of Pa.

[73] Assignee: Gulf Research & Development Company, Pittsburgh, Pa.

[21] Appl. No.: 972,929

[22] Filed: Dec. 26, 1978

[51] Int. Cl.$^2$ .................... C07F 15/00; C01G 55/00; B01J 23/96; B01J 31/18

[52] U.S. Cl. .............................. 260/429 R; 252/412; 252/414; 252/416; 252/431 N; 423/22; 423/592; 423/593; 568/860

[58] Field of Search ................... 252/412, 414, 416; 568/860; 423/22, 593; 260/429 R

[56] References Cited

U.S. PATENT DOCUMENTS

| | | | |
|---|---|---|---|
| 3,317,592 | 5/1967 | MacLean et al. ................ | 252/412 |
| 4,049,724 | 9/1977 | Sheng et al. ................ | 568/860 |

*Primary Examiner*—P. E. Konopka

[57] ABSTRACT

Osmium (III) or (IV) in an anionic complex with oxygen and having an alkali metal, ammonium or tetra(-lower)alkylammonium cation is oxidized to a valency state higher than 5 by reaction with an organic hydroperoxide, such as ethylbenzene hydroperoxide, at a temperature less than 30° C.

12 Claims, No Drawings

METHOD OF OXIDIZING OSMIUM (III) AND OSMIUM (IV) TO A HIGHER VALENCY STATE

SUMMARY OF THE INVENTION

This invention relates to a procedure for oxidizing osmium in an ionic complex at a valency state lower than 5 to a valency state higher than 5 using a hydroperoxide such as ethylbenzene hydroperoxide.

We have, in particular, discovered a process for regenerating an osmium catalyst comprising an ionic complex of osmium in the 8 valency state which has been deactivated by the reduction of the osmium to a non-catalytic valency state lower than 5 by contacting the deactivated catalyst with a hydroperoxide at a reduced temperature.

DESCRIPTION OF THE INVENTION

Olefins such as ethylene and propylene can be hydroxylated to the corresponding glycol using a relatively stable hydroperoxide in the presence of osmium tetroxide and a strong base such as a tetra(lower)alkylammonium hydroxide and cesium hydroxide. Some or all of the osmium tetroxide reacts with the strong base to form the ionic complex of the osmium (VIII). In this hydroxylation reaction the osmium (VIII) compound functions as an oxidant while it concurrently is reduced to a catalytically inactive osmium (VI) compound. But the hydroperoxide then instantly oxidizes the osmium (VI) compound back to the active osmium (VIII) compound. This in situ conversion of the osmium (VI) back to the osmium (VIII) continues as long as there is unreacted hydroperoxide in the reactor.

Because of the great expense of osmium, the osmium must be recovered and recycled in the process. However, the osmium quickly loses its utility as a catalyst as the result of declining activity over a relatively few cycles. This results because some of the osmium is reduced to a valency state lower than 5, probably osmium (III) and/or osmium (IV), which is catalytically inactive and, unlike the osmium (VI), is not regenerated back to osmium (VIII) in the hydroxylation reactor. Therefore, this inactive lower valency state osmium builds up after several cycles until the osmium loses its usefulness as a catalyst.

We have discovered that these valency states of osmium in the ionic complex which are lower than 5 can be raised to a valency state higher than 5, if the purified ionic complex of osmium is contacted with a stable secondary or tertiary organic hydroperoxide at subambient temperatures, that is, temperatures less than 30° C. Under these conditions the osmium is oxidized to a valency higher than 5, probably substantially completely to Os(VIII). If ambient or superambient temperatures are used, the osmium catalyzes the decomposition of the hydroperoxide without significant oxidation of the osmium to a higher valency state.

The process of our invention relates to ionic osmium compounds having the general formula $M_xOsO_y$ in which M is alkali metal including lithium, sodium, potassium, rubidium and cesium; ammonium or tetra(lower)alkylammonium in which the alkyl group has from one to about four carbon atoms; and 2y-x is the valence of the osmium in the compound. In accordance with our process the valence of the osmium in any compound defined by this formula, whether pure or as part of a mixture of compounds defined by this formula, which is less than 5 can be increased to a valence greater than 5 by treating the osmium compound or mixture of osmium compounds with the hydroperoxide at subambient temperatures. Thus, the osmium (III) compound, $MOsO_2$, and the osmium (IV) compound, $M_2OsO_3$, are oxidized to the osmium (VI) compound, $M_2OsO_4$, known as the osmate, and this is further oxidized to the catalytically active osmium (VIII) compound, $M_2OsO_5$, which is known as the perosmate.

Since many organic compounds will reduce osmium (VIII) to a lower valency state, it is essential that any organic compound which will reduce osmium (VIII) be excluded from the reaction zone in which the osmium catalyst is regenerated. If this is not done the regeneration is ineffective or only partially effective. It is for this reason that the organic components in the hydroxylation reaction product are substantially completely removed from the osmium catalyst residue before it is regenerated.

Any organic secondary and tertiary hydroperoxide, which is substantially stable, at the subambient temperature used in the regeneration can be used for the regeneration reaction. This includes hydroperoxides such as ethylbenzene hydroperoxide, cumene hydroperoxide, t.butyl hydroperoxide, t.pentyl hydroperoxide, 1-phenyl cyclohexyl hydroperoxide, and the like. We have attempted to regenerate a deactivated osmium catalyst with hydrogen peroxide at a subambient temperature and discovered that the hydrogen peroxide was completely decomposed without catalyst regeneration.

Since the hydroperoxide is generally prepared by the partial oxidation of its hydrocarbon precursor, the hydroperoxide can be used in the regeneration reaction in solution with its precursor compound, such as ethylbenzene hydroperoxide in ethylbenzene. Or the hydroperoxide can be used in solution in a solvent which is not oxidizable by the osmium (VIII) compound, such as t.butyl hydroperoxide in t.butanol or water.

The present process for the oxidation of osmium in ionic compounds and for the regeneration of ionic osmium catalysts is carried out at a temperature below about 30° C., since osmium catalyzes the significant undesired decomposition of hydroperoxides at about 30° C. and higher. Therefore, the present process is carried out at a temperature less than 30° C., preferably a temperature between about −10° C. and about 25° C., and most preferably a temperature between about 0° C. and about 20° C.

DESCRIPTION OF PREFERRED EMBODIMENTS

Example 1

A charge of 100 ml. of t.butanol and 7.5 ml. of ten percent aqueous tetraethylammonium hydroxide was placed in a 300 ml. thickwalled glass reactor equipped with a thermocouple and a stirring magnet. The solution was cooled to 0° C. in an ice-salt bath. After adding 59 g. of twenty percent ethylbenzene hydroperoxide in ethylbenzene (80 mmols) to the chilled solution, the reactor was sealed. Ethylene was introduced into the reactor to a pressure of about 120 psi. Then 5 ml. of 0.5 percent osmium tetroxide (0.1 mmol) in t.butanol was pressured into the reactor in a stream of ethylene. The ethylene pressure was adjusted to 150 psi. and the reaction was allowed to proceed for six hours at 0° C. and at about 150 psi (1.03 MPa). The reactor was then permitted to stand overnight at room temperature. The reaction product was analyzed by gas-liquid chromatography and showed 3.34 g. of ethylene glycol (53.8 mmols) which was a 67.3 percent yield of ethylene glycol based on the ethylbenzene hydroperoxide charged.

Example 2

The reaction product from Example 1 was evaporated at 90° C. and a pressure of five mm. to remove most of the organic components. The residue (less than 5 ml.) containing osmium catalyst was diluted to 100 ml. with t.butanol and mixed with 7.5 ml. of a 10 percent aqueous solution of tetraethylammonium hydroxide. The solution was placed in a glass reactor and cooled to 0° C. The reactor was sealed and pressured to 120 psi. with ethylene. Then 59 ml. of 20 percent ethylbenzene hydroperoxide (80 mmols) was introduced from a charge tube connected to the glass reactor by means of extra ethylene pressure. The ethylene pressure was adjusted to 150 psi. and maintained at this pressure. The reaction was run for 6 hours at 0° C. and left overnight at room temperature. The unreacted ethylene was vented and the reaction product was analyzed by gas-liquid chromatography and was found to contain 2.87 g. of ethylene glycol, a 57.9 percent yield of ethylene glycol. The catalyst residue from this example was recovered in the same manner and reused as described in this example for a series of catalyst recovery and recycle runs without catalyst regeneration. The results are set out in Table I

Example 3

The procedures of Example 1 were repeated with fresh catalyst. The reaction product analyzed 3.16 g. of ethylene glycol, a yield of 63.6 percent ethylene glycol based on the ethylbenzene hydroperoxide charged.

Example 4

The reaction product from Example 3 was evaporated at 90° C. and a pressure of five mm. to remove most of the organic components. There was obtained less than five ml. of a residue of the osmium catalyst. It was cooled to 0° C. and stirred with 10 ml. of 20 percent ethylbenzene hydroperoxide for 4 hours. The mixture was warmed to room temperature and left standing overnight. Next morning a small sample of the mixture was titrated iodometrically to make sure there was no unreacted ethylbenzene hydroperoxide left. The color of the catalyst mixture had changed from dark brown to brownish yellow. The catalyst mixture was diluted to 100 ml. with t.butanol and mixed with 7.5 ml. 10 percent aqueous solution of tetraethylammonium hydroxide. The solution was placed in a glass reactor and cooled to 0° C. The reactor was sealed and pressured to 120 psi. with ethylene. The 59 ml. of 20 percent ethylbenzene hydroperoxide (80 mmols) was introduced from a charge tube connected to the reactor by means of extra ethylene pressure. The ethylene pressure was adjusted to 150 psi. and maintained at this pressure. The reaction was run for 6 hours at 0° C. and left overnight at room temperature. The reaction product was analyzed by gas-liquid chromatography and found to contain 3.24 g. of ethylene glycol, a yield of 65.3 percent. The catalyst residue from this example was recovered and regenerated in the same manner and reused as described in this example for a series of catalyst recovery and recycle runs. These results are also set out in Table I.

Table 1

| Run | Ethylene glycol, without regeneration | | Ethylene glycol, with regeneration | |
|---|---|---|---|---|
| | Wt.,g. | Yield % | Wt.,g. | Yield, % |
| Original | 3.34 | 67.3 | 3.16 | 63.6 |
| 1st recycle | 2.87 | 57.9 | 3.24 | 65.3 |
| 2nd recycle | 1.98 | 39.9 | 3.02 | 60.8 |
| 3rd recycle | 0.80 | 16.0 | 3.12 | 62.9 |
| 4th recycle | 0.10 | 2.0 | 3.10 | 62.5 |
| 5th recycle | — | — | 3.13 | 63.0 |
| 6th recycle | — | — | 2.79 | 56.1 |

This process can also be used to oxidize the osmium in an oxide of osmium having a valency state less than 5, such as $OsO_2$ and $Os_2O_3$. In this modification the oxide of osmium having a valency state less than 5 is dissolved in a solution of an alkali metal hydroxide, ammonium hydroxide or tetra(lower)alkylammonium hydroxide. The hydroxide solution can be an aqueous solution or an organic solution can be used if the hydroxide is soluble in the organic solvent, such as tetraethylammonium hydroxide in t.butanol. When this solution is contacted with the organic hydroperoxide, the valency state of the osmium is increased. The resulting solution can then be neutralized and the osmium oxide of higher valency state can be recovered.

It is to be understood that the above disclosure is by way of specific example and that numerous modifications and variations are available to those or ordinary skill in the art without departing from the true spirit and scope of the invention.

We claim:

1. The method for oxidizing osmium in an ionic complex from a valency state less than 5 to a valency state greater than 5 which comprises contacting an ionic complex of osmium having the general formula $M_xOsO_y$ in which M is alkali metal, ammonium, or tetra(lower)alkylammonium and 2y-x is less than 5 with an organic secondary or tertiary hydroperoxide at a temperature less than about 30° C.

2. The method for oxidizing osmium in an ionic complex from a valency state less than 5 to a valency state greater than 5 in accordance with claim 1 wherein the said ionic complex of osmium having a valency state less than 5 is a deactivated catalyst.

3. The method for oxidizing osmium in an ionic complex from a valency state less than 5 to a valency state greater than 5 in accordance with claim 2 wherein M is cesium, rubidium or potassium.

4. The method for oxidizing osmium in an ionic complex from a valency state less than 5 to a valency state greater than 5 in accordance with claim 2 wherein M is tetra(lower)alkylammonium.

5. The method for oxidizing osmium in an ionic complex from a valency state less than 5 to a valency state greater than 5 in accordance with claim 2 wherein an ionic complex of osmium having the formula $M_2OsO_5$ is recovered.

6. The method for oxidizing osmium in an ionic complex from a valency state less than 5 to a valency state greater than 5 in accordance with claim 1 which comprises contacting an ionic complex of osmium (III) or osmium (VI) or a mixture thereof.

7. The method for oxidizing osmium in an ionic complex from a valency state less than 5 to a valency state greater than 5 in accordance with claim 1 wherein the said temperature is between about −10° C. and about 25° C.

8. The method for oxidizing osmium in an ionic complex from a valency state less than 5 to a valency state greater than 5 in accordance with claim 2 wherein the said temperature is between about 0° C. and about 20° C.

9. The method for oxidizing osmium in an ionic complex from a valency state less than 5 to a valency state greater than 5 in accordance with claim 2 wherein the said organic hydroperoxide is ethylbenzene hydroperoxide, cumene hydroperoxide, t.butyl hydroperoxide, t.pentyl hydroperoxide or 1-phenyl cyclohexyl hydroperoxide.

10. The method for oxidizing osmium in an ionic complex from a valency state less than 5 to a valency state greater than 5 in accordance with claim 1 wherein the said ionic complex of osmium is formed by dissolving an oxide of osmium having a valency state less than 5 in a solution of the hydroxide of said alkali metal, ammonium or tetra(lower)alkylammonium.

11. The method for oxidizing osmium in an ionic complex from a valency state less than 5 to a valency state greater than 5 in accordance with claims 1 or 10 wherein the product solution is neutralized and an oxide of osmium having a valency state greater than 5 is recovered therefrom.

12. The method for oxidizing osmium in an ionic complex from a valency state less than 5 to a valency state greater than 5 in accordance with claim 1 wherein said contacting is carried out in the substantial absence of any organic compound which will reduce osmium (VIII).

* * * * *

UNITED STATES PATENT OFFICE
CERTIFICATE OF CORRECTION

Patent No. 4,217,291              Dated  August 12, 1980

Inventor(s) Ching-Yong Wu and Thaddeus P. Kobylinski

It is certified that error appears in the above-identified patent and that said Letters Patent are hereby corrected as shown below:

Column 4, line 63, "(VI)" should read --(IV)--.

Signed and Sealed this

Twenty-eighth Day of October 1980

[SEAL]

Attest:

Attesting Officer

SIDNEY A. DIAMOND

Commissioner of Patents and Trademarks